(12) United States Patent
Kim et al.

(10) Patent No.: US 9,987,475 B2
(45) Date of Patent: Jun. 5, 2018

(54) MICRO NEEDLE ROLLER ASSEMBLY

(75) Inventors: Chang-hyun Kim, Daejeon-si (KR);
Dong-hun Hyun, Daejeon-si (KR);
Seung-sup Lee, Daejeon-si (KR);
Man-hee Han, Daejeon-si (KR)

(73) Assignees: LOTTE CHEMICAL CORPORATION (KR); KOREA ADVANCED INSTITUTE OF SCIENCE AND TECHNOLOGY (KR)

( * ) Notice: Subject to any disclaimer, the term of this patent is extended or adjusted under 35 U.S.C. 154(b) by 1003 days.

(21) Appl. No.: 12/307,315

(22) PCT Filed: Jun. 27, 2007

(86) PCT No.: PCT/KR2007/003121
§ 371 (c)(1),
(2), (4) Date: Jan. 2, 2009

(87) PCT Pub. No.: WO2008/004781
PCT Pub. Date: Jan. 10, 2008

(65) Prior Publication Data
US 2009/0312691 A1 Dec. 17, 2009

(30) Foreign Application Priority Data

Jul. 3, 2006 (KR) .......... 10-2006-0061787
Jul. 3, 2006 (KR) .......... 10-2006-0061788
Feb. 9, 2007 (KR) .......... 10-2007-0013559

(51) Int. Cl.
*A61M 37/00* (2006.01)
*A61H 15/00* (2006.01)
(Continued)

(52) U.S. Cl.
CPC ..... *A61M 37/0015* (2013.01); *A61H 15/0092* (2013.01); *A61H 23/0263* (2013.01);
(Continued)

(58) Field of Classification Search
CPC .... A61H 2015/0007; A61H 2015/0014; A61H 2015/0071; A61H 15/0092;
(Continued)

(56) References Cited

U.S. PATENT DOCUMENTS 4,011,622 A * 3/1977 Gillum ............... B05C 17/0222
15/248.2
4,625,366 A * 12/1986 Egerer ..................... D01H 4/32
19/112
(Continued)

FOREIGN PATENT DOCUMENTS

JP 3042081 7/1997
JP 3055522 10/1998
(Continued)

OTHER PUBLICATIONS

International Search Report dated Sep. 27, 2007, issued in corresponding international application No. PCT/KR2007/003121.
(Continued)

*Primary Examiner* — Kami A Bosworth
*Assistant Examiner* — Shefali Patel
(74) *Attorney, Agent, or Firm* — Ostrolenk Faber LLP (57) ABSTRACT

The present invention provides a micro needle roller assembly comprising a roller head including an external cylindrical member having a plurality of micro needles mounted on a surface thereof and an internal member placed in the external member and supported to the external member by supporting pieces; and a handling member coupled to the internal member for rotating the internal member of the roller head; the plurality of micro needles, the external cylindrical member and the internal member being made of a polymer resin.

20 Claims, 8 Drawing Sheets

(51) Int. Cl.
*A61H 23/02* (2006.01)
*A61N 5/06* (2006.01)

(52) U.S. Cl.
CPC ............... *A61H 2015/0014* (2013.01); *A61H 2201/0173* (2013.01); *A61H 2201/0176* (2013.01); *A61H 2201/10* (2013.01); *A61H 2201/1685* (2013.01); *A61H 2201/1695* (2013.01); *A61H 2201/5082* (2013.01); *A61M 2037/0023* (2013.01); *A61M 2037/0046* (2013.01); *A61M 2037/0061* (2013.01); *A61N 2005/066* (2013.01); *A61N 2005/0644* (2013.01)

(58) Field of Classification Search
CPC ........ A61H 2201/10; A61H 2201/1685; A61H 2201/1695; A61M 37/0015; A61M 2037/0023; A61M 2037/0046; A61N 2005/0644; A61N 2005/0659; A61N 2005/066
USPC ............................................ 604/22, 20, 272
See application file for complete search history.

(56) References Cited

U.S. PATENT DOCUMENTS

| | | | |
|---|---|---|---|
| 6,334,856 B1 * | 1/2002 | Allen | A61B 5/1411 128/898 |
| 6,648,904 B2 * | 11/2003 | Altshuler et al. | 607/96 |
| 2003/0153900 A1 * | 8/2003 | Aceti | A61B 5/1411 604/890.1 |
| 2006/0051404 A1 * | 3/2006 | Yeshurun et al. | 424/449 |
| 2006/0091584 A1 * | 5/2006 | Lyapko | 264/237 |
| 2006/0197370 A1 | 9/2006 | Mercat | 301/59 |
| 2006/0206062 A1 * | 9/2006 | Naimark | A61M 25/0069 604/264 |
| 2007/0288078 A1 * | 12/2007 | Livneh | A61B 18/1477 607/147 |
| 2008/0214987 A1 * | 9/2008 | Xu | A61K 9/0021 604/21 |

FOREIGN PATENT DOCUMENTS

| | | | | |
|---|---|---|---|---|
| JP | 2002-159339 | 6/2002 | | |
| JP | 2003-47526 | 2/2003 | | |
| JP | 2003-529401 | 10/2003 | | |
| JP | 2005-503210 | 2/2005 | | |
| KR | 20-0115807 | 12/1997 | | |
| KR | 20-0418106 Y1 | 6/2006 | | |
| KR | 20-0428914 Y1 | 10/2006 | | |
| WO | WO 02/047555 A3 | 6/2002 | | |
| WO | WO 02/49711 A1 | 6/2002 | | |
| WO | WO 0247555 A2 * | 6/2002 | ......... A61H 15/0092 | |
| WO | WO 2005/082596 A1 | 9/2005 | | |
| WO | WO 2006/020841 | 2/2006 | | |

OTHER PUBLICATIONS

Office Action issued in corresponding Japanese Patent Application No. 2009-506425 dated Apr. 5, 2011 (4 pages).

* cited by examiner

MICRO NEEDLE ROLLER ASSEMBLY

CROSS REFERENCE TO RELATED APPLICATIONS

The present application is a 35 U.S.C. § 371 National Phase conversion of PCT/KR2007/003121, filed Jun. 27, 2007, which claims benefit of Korean Application No. 10-2006-0061787, filed Jul. 3, 2006, Korean Application No. 10-2006-0061788, filed Jul. 3, 2006 and Korean Application No. 10-2007-0013559, filed Feb. 9, 2007. The PCT International Application was published in the English language.

TECHNICAL FIELD

The present invention relates to a micro needle roller assembly, more particularly, to a micro needle roller assembly utilized for delivering drug through a skin tissue.

BACKGROUND ART

In general, in the method for transdermal delivery of drug, drug is difficult to penetrate stratum corneum, and so an absorptance of drug is extremely low. In particular, the larger a molecular weight of drug is, the less a drug absorptance becomes. In order to remove the aforementioned problem, the technology utilizing micro needles has been proposed. In this technology, channels penetrating a portion or all of epidermis of the skin are formed by the micro needles and drug is then delivered to the epidermis of the skin or a underlayer of the epidermis through the channels.

According to the above technology utilizing micro needles, the drug having a large molecular weight, such as insulin, hormone medicine and the like can be easily delivered. In addition, once the micro needles penetrate and stimulate the dermis of the skin, a burn or a scar can be naturally healed. Also, a generation of the collagen is induced so that it is possible to improve the skin tone and maximize an anti-aging effect.

In current, a micro needle roller is utilized as a channel forming means. The micro needle roller comprises a cylindrical roller head on which a plurality of micro needles are formed, the micro needles form a plurality of channels on the skin when the roller head is rotated. Examples of the micro needle roller are disclosed in WO02/47555, WO02/49711.

In the above conventional micro needle roller, however, the micro needles are made of stainless steel. And, the micro needles are protruded from an inside of the roller head, and so a space in which the needles can be disposed is limited. Consequently, there is a limit to a reduction of a distance between the needles.

In general, a linear distance between the needles are approximately 2 mm, it is difficult to reduce the distance between the needles to maximize the treatment effect. In addition, to utilize repeatedly the needle roller, the needle roller should be sterilized. Also, since the needle roller is made of stainless steel, its manufacturing cost and selling price become high.

As another related art, the tool for forming channel on skin for delivery drug comprising circular shaped thin plates, each of which having a plurality of skin needles formed at an end portion thereof, spacers, each of which being disposed between the thin plates, a central axis on which the thin plates and the spacers are assembled and reinforcing members mounted to both ends of the central axis is disclosed in Korean Utility Registration No. 115807.

However, the above tool has the problem that the process for manufacturing this device is complicated so that it is difficult to manufacture the device in large quantities at extremely low cost. For example, the circular shaped thin plates should be alternatively assembled, and so there is a difficulty manufacturing this tool due to the above condition. Accordingly, there are drawbacks that the above tool can not be manufactured through one shot process and a manufacturing time becomes lengthened.

DISCLOSURE OF INVENTION

Technical Problem

Accordingly, the present invention is conceived to solve the aforementioned problems of the conventional micro roller assembly, an object of the present invention is to provide a micro roller assembly which has a simple structure and is able to shorten a manufacturing time and can be manufactured in a mass production manner with a low manufacturing cost.

Another object of the present invention is to provide a micro needle roller assembly which can enhance the drug transdermal delivery efficiency due to a narrow distance between needles.

Technical Solution

In order to achieve the above objects, a micro needle roller assembly according to the present invention comprises a roller head including an external cylindrical member having a plurality of micro needles mounted on a surface thereof and an internal member placed in the external member and supported to the external member by supporting piece; and a handling member coupled to the internal member for rotating the internal member of the roller head; the micro needles, the external cylindrical member and the internal member being made of polymer resin.

Here, the internal member is a hollow cylindrical member and the supporting pieces are extended in a radial direction of the internal member. Also, the internal member has cylindrical shaped receiving spaces formed at both end portions thereof.

The micro needles, the external cylindrical member and the internal member are made of polymer resin such thermosetting resin or thermoplastic resin and can be formed integrally with each other.

On the other hand, the handling member comprises a gripper; first and second connecting arms extended from the gripper; and protrusions formed on inner surfaces of the first and second connecting arms, the protrusions being received in the receiving spaces formed at both end portions of the internal member of the roller head.

Also, the external member of the roller head has grooves formed on a surface thereof, the roller head comprises needle blocks having needles formed thereon, and the needle blocks are received in the grooves.

Here, the groove is extended in the longitudinal direction of the external member and has an upper portion and a lower portion having a width larger than that of the upper portion, and the needle block has a sectional shape that is the same as that of the groove.

In particular, the grooves can be formed in parallel to an axis of the external cylindrical member. On the contrary, the grooves are inclined at a certain angle with respect to an axis of the external cylindrical member.

The micro needle roller assembly according to the present invention can further comprises side covers fixed to both side ends of the roller head, each side cover has an opening corresponding to the internal member.

The micro needle roller assembly according to the present invention can further comprises a vibration generating means and a power electric source received in a space formed in the gripper of the handling member.

The micro needle roller assembly according to the present invention may further comprise a cover fixed to the gripper and placed on the roller head.

Advantageous Effects

Since all structural members, that is, the cylindrical external member and a plurality of needles formed on an outer surface of the external member and the internal member coupled to the external member by the supporting pieces are made of polymer resin and formed integrally with each other, the micro needle roller assembly according to the present invention can be simply manufactured by only once injection forming process.

In addition, in the micro needle roller assembly according to the present invention, the needle blocks on which the micro needles are formed and the roller head are separately manufactured and then assembled to each other. Accordingly, after the needle blocks that were contacted with the user's skin are detached from the roller head, new needle blocks are be then mounted to the roller head so that the roller head and the handling member can be repeatedly utilized.

Further, a plurality of needles having the different size (diameter and height) can be formed the needle blocks, respectively, and so the user can select the needle block having a desired sized needles on the basis of the kind of drug, a dosage of drug and a part of the body to which the drug is applied, and then mount the selected needle block to the roller head.

In particular, since the micro needle roller assembly according to the present invention comprises a vibration generating means, the micro needles pierces effectively skin due to a vibration transmitted to the roller head so that the drug delivery effect is increased, the skin tissue is activated and a circulation of blood can be expedited.

In addition, when the micro needles pierce the skin, blood spurted from channels formed by the needles is blocked by the cover placed on the roller head, and so the use can use sanitarily the micro roller assembly.

In particular, the skin can become soft by infrared ray radiated from the infrared ray-generating device to stimulate the skin contacted with the micro needles. Accordingly, the drug may be delivered in the skin to enhance remarkably a treatment effect.

BRIEF DESCRIPTION OF THE DRAWINGS

The above and other objects, features and advantages of the present invention will become apparent from the following description of preferred embodiments given in conjunction with the accompanying drawings, in which.

BEST MODE FOR CARRYING OUT THE INVENTION

Hereinafter, the micro needle roller assembly according to the preferred embodiments of the present invention will be described in more detail with reference to the accompanying drawings.

First Embodiment

Figure 1:
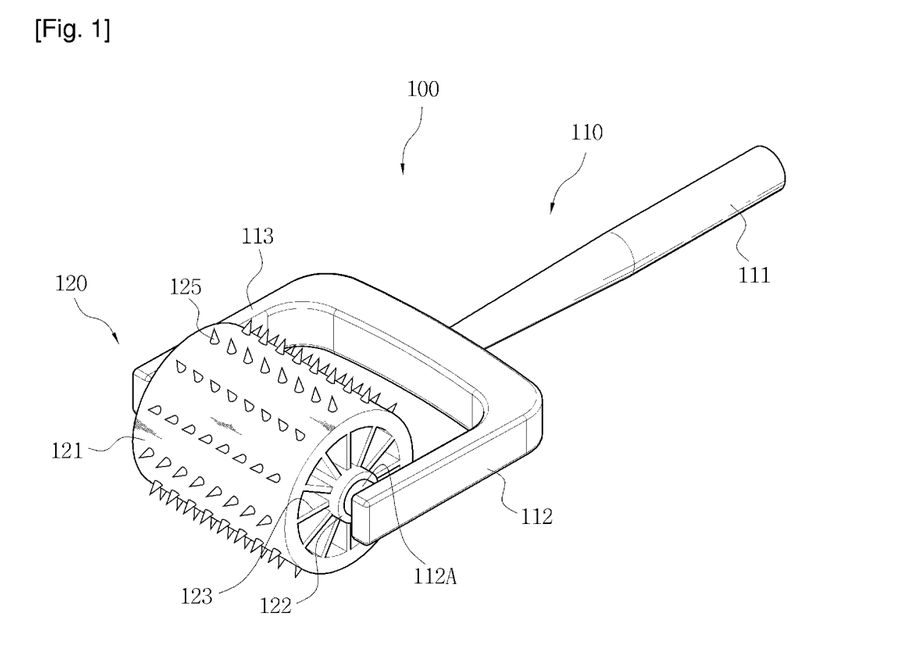
FIG. 1 is a perspective view of a micro needle roller assembly according to the first embodiment of the present invention.
Figure 2:
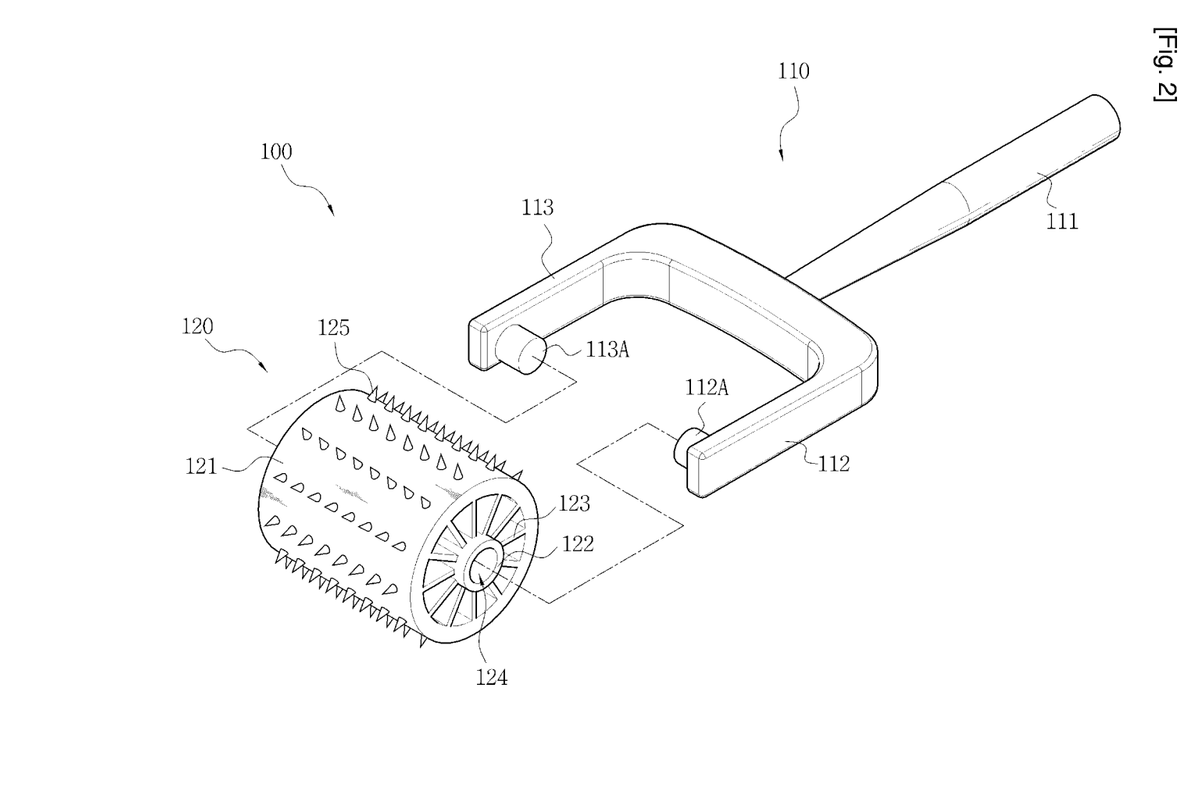
FIG. 2 is an exploded perspective view of the micro needle roller assembly according to the first embodiment of the present invention.

FIG. 1 is a perspective view of a micro needle roller assembly according to the first embodiment of the present invention and FIG. 2 is an exploded perspective view of a micro needle roller assembly according to the first embodiment of the present invention.

Referring to FIG. 1 and FIG. 2, a micro needle roller assembly 100 (hereinafter, referred to as "needle roller assembly" comprise a roller head 120 and a handling member 110.

The roller head 120 comprises an external hollow cylindrical member 121 (hereinafter, referred to as "external member") and an internal hollow member 122 (hereinafter, referred to as "internal member") placed in the external member 121. The internal member 122 is supported to the external member 121 by a plurality of supporting pieces 123 fixed thereto and extended in a radial direction. The number of the supporting pieces 123 and a length of each supporting piece are not limited. However, it is preferred that a length of each supporting piece 123 is the same as that of the external member 121 so as to prevent the external member 121 from being transformed when the force is applied to the external member.

The external member 121 and the internal member 122 are coaxially disposed and a shape of the internal member is not limited to a specific one. A receiving space 124 of the internal member 122 is utilized as a space for receiving a specific member constituting the handling member 110 described below.

A plurality of micro needles 125 (hereinafter, referred to as "needle" are formed on an outer surface of the external member 121. Preferably, the external member 121 and the needles 125 of the roller head 120 are formed integrally with each other and made of polymer resin such as thermosetting resin including epoxy resin, phenol resin, polyurethane resin or thermoplastic resin including PC (polycarbonate), PEI (polyetherimide), PMMA (polymethylmethacrylate), POM (polyacetal), PLA (polylatide), PSU (polysulfone) and the like.

Here, it is preferred to use biodegradable polymer, for example PLA (polylatide), PLGA (poly lactic-co-glycolic acid) as polymer resin. Due to the above material, if the needle 125 is remained in the skin, the needle made of the above mentioned material does not harm human being and can be dissolved in short time, Each needle 125 is protruded from an outer surface of the external member 121 with a certain height. A height of the needle 125 may be varied according to a usage of the micro needle roller assembly 100. For example, if the needle 125 penetrates an epidermis to form a channel reaching a corium layer, a height of the needle 125 is in the range from 200 µm to 750 µm. In general, a height of the needle 125 is determined in the range from 20 µm to 2,000 µm, however, a height of the needle can be out of the above range, if necessary.

On the other hand, the needles 125 can be disposed on an outer surface of the external member 121 with lines at regular intervals. Due to the above structure, the uniform channel distribution can be obtained on a specific area of the skin. However, in order to form a great number of the channels on a specific area of the skin through the needles 125, it is desirable to make narrow a distance between the lines constituting the needles 125 on an outer surface of the external member 121 within the limits of the possible.

In addition, FIG. 2 shows that each needle 125 has a conical shape. However, a shape of the needle is not limited thereto.

Figure 3:
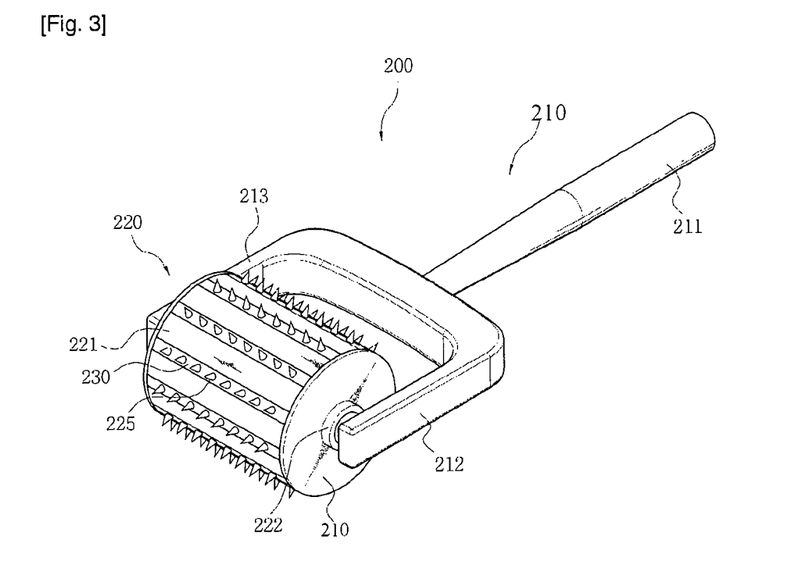
FIG. 3 is a perspective view of the micro needle roller assembly according to the second embodiment of the present invention.

Unlike the roller head shown in FIG. 3, on the other hand, the roller may be constituted by using only one cylindrical member having a cylindrical space formed at a central portion thereof. However, it is inevitable that the roller head having the above structure has a large volume, and so material mentioned previously is significantly influenced by heat during a forming process for manufacturing the roller head In view of the above, the roller head 120 according to this embodiment consists of the internal member 122, the external member 121 and a plurality of supporting pieces 123 connecting both members, and so an entire volume of the roller head is remarkably reduced, whereby it is possible to reduce significantly a transformation caused by heat in the forming process.

In particular, in micro needle roller assembly according to this embodiment of the present, the cylindrical external member, a plurality of needles formed on an outer surface of the cylindrical external member and the internal member are made of polymer resin and formed integrally with each other, and the roller head can be formed by performing only once injection forming process.

On the other hand, the handling member 110 comprises a gripper 111 and first and second connecting arms 112 and 113 extended from one end of the gripper to both sides. Free ends of the first and second connecting arms 112 and 113 correspond to both side ends of the internal member 122 of the roller head 120. Cylindrical protrusions 112A and 113A with a certain length are protrudely formed on inner surfaces of the free end portions of the first and second connecting arms 112 and 113, respectively, By inserting the cylindrical protrusions 112A and 113A formed on inner surfaces of the free end portions of the first and second connecting arms 112 and 113 into both side ends of the receiving space 124 of the internal member 122 of the roller head 120, an assembling of the handling member 110 and the roller head 120 is completed.

A diameter of each of the protrusions 112A and 113A is smaller than that of the receiving space 124 of the internal member 122, and so each of the protrusions 112A and 113A can be rotated in the receiving member of the internal member 122.

On the other hand, in order to insert easily the protrusions 112A and 113A into the receiving space 124 of the internal member 122 and to inhibit the protrusions 112A and 113A from being taken out of the receiving space 124 after the protrusions are inserted in the receiving space, it is preferred that the first and second coupling arms 112 and 113 of the handling member 110 are made of material having an elasticity.

Below, the function of the needle roller assembly 100 according to this embodiment constructed as described above is described with reference to the drawings.

As described above, the protrusions 112A and 113A formed on the first and second connecting arms 112 and 113 of the handling member 110 are inserted into both end portions of the receiving space 124 of the internal member 122 of the roller head 120 to assemble the handling member 110 and the roller head 120.

Then, the user grips the griper 111 of the handling member 110 and places the external member 121 of the roller head 120 on a skin. At this time, the transdermal drug is already applied on the skin.

In this state, once the user exerts a force on the gripper 111, the roller head 120 is rotated about the protrusions 112A and 113A received in the receiving space 124 and moved on the skin.

Due to a rotation and movement of the roller head 120 on the skin, the needles 125 formed on the external member 121 penetrate a portion of epidermis or entire epidermis constituting the skin to form delivery paths (channels) for the transdermal drug. In the above process, the transdermal drug applied on the skin penetrates the skin through the channel formed by the needles 125.

On the other hand, as described above, the internal member 122 of the roller head 120 does not have to be formed into a cylindrical shape if the receiving space 124 in which the protrusions 112A and 113A formed on the first and second connecting arms 112 and 113 is received and rotated has a cylindrical shape. In addition, although the above description illustrates that the receiving space 124 is formed along the entire length of the internal member 122, the space can be formed in each of both end portions of the internal member 122.

Second Embodiment

Figure 4:
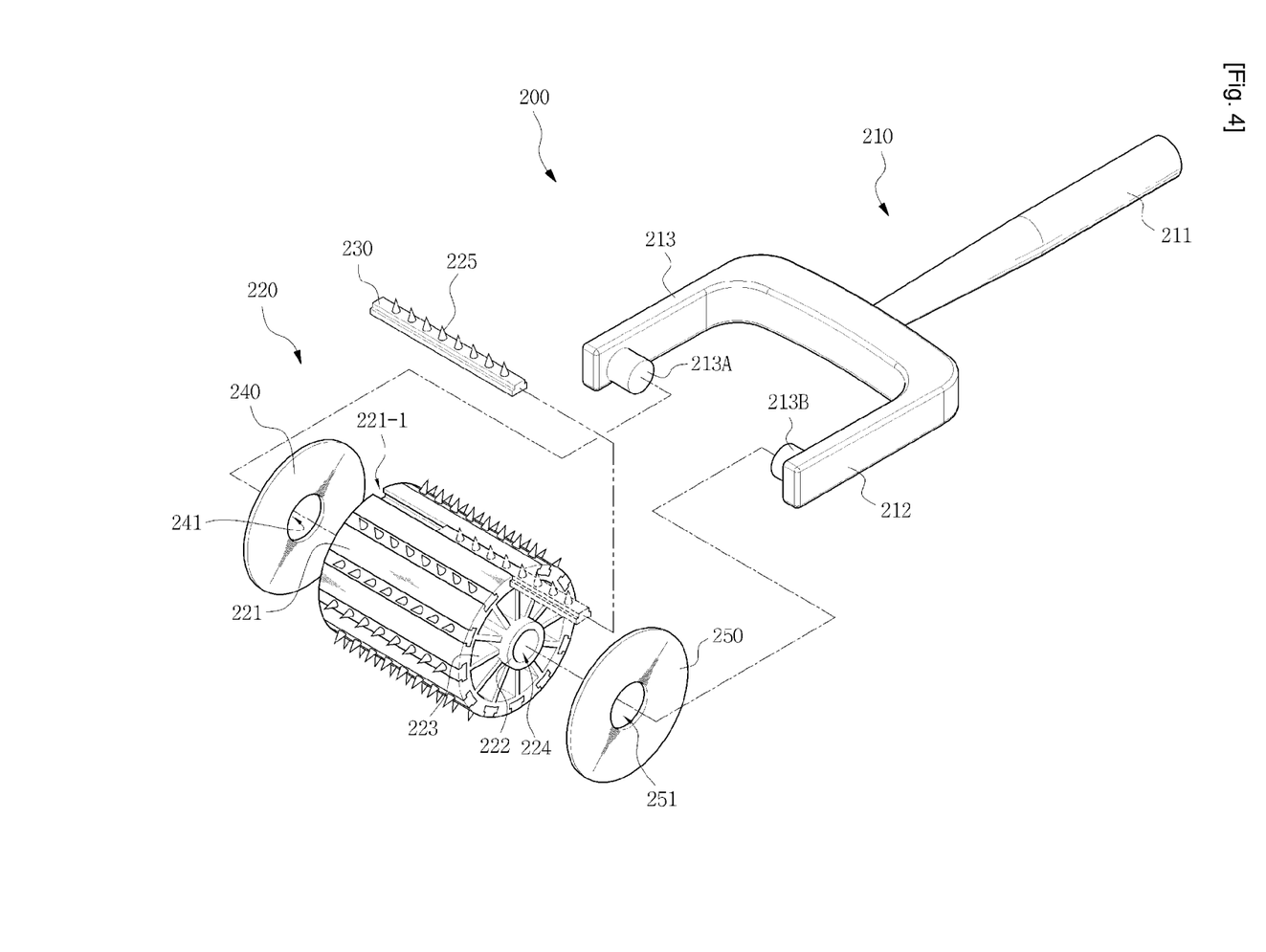
FIG. 4 is an exploded perspective view of the micro needle roller assembly according to the second embodiment of the present invention.

FIG. 3 and FIG. 4 are perspective view and exploded perspective view of a micro needle roller assembly according to the second embodiment of the present invention and show the structure of each of the members constituting the micro needle roller assembly according to the second embodiment of the present invention.

Referring to FIG. 3 and FIG. 4, a micro needle roller assembly 200 (hereinafter, referred to as "needle roller assembly") also comprise a roller head 220 and a handling member 210.

The handling member 210 comprises a gripper 211 and first and second connecting arms 212 and 213 extended from one end of the gripper to both sides. Free ends of the first and second connecting arms 212 and 213 correspond to both side ends of an internal member 222 of the roller head 220. Cylindrical protrusions 212A and 213A with a certain length are protrudely formed on inner surfaces of the free end portions of the first and second connecting arms 212 and 213, respectively, A structure and function of each element constituting the handling member 210 are the same as those of each element constituting the handling member 110, and so the description thereof is omitted.

The roller head 220 in the needle roller assembly 200 according to the present embodiment comprises an external hollow cylindrical member 221 (hereinafter, referred to as "external member" and an internal hollow member 222 (hereinafter, referred to as "internal member" placed in the external member 221. The internal member 222 is supported to the external member 221 by a plurality of supporting pieces 223 fixed thereto and extended in a radial direction.

A structure and relation of the external member 221 and the internal member 222 in this embodiment are the same as those of the external member and the internal member in the first embodiment, and so the description thereof is omitted.

In addition, a plurality of needle blocks 230 are mounted on an outer surface of the external member 221 of the roller head 220. Structures of the roller head 200 and needle block are concretely described with reference to FIG. 4 and FIG. 5 as follows.

As shown in FIG. 4, the roller head 220 consists of the external hollow cylindrical member 221 and the internal hollow member 222, a plurality of grooves 222-1 having a certain length are formed on an outer surface of the external member 121. Both ends of each groove 221-1 are opened, and a width of an upper portion of each groove is smaller than that of a lower portion.

Figure 5:
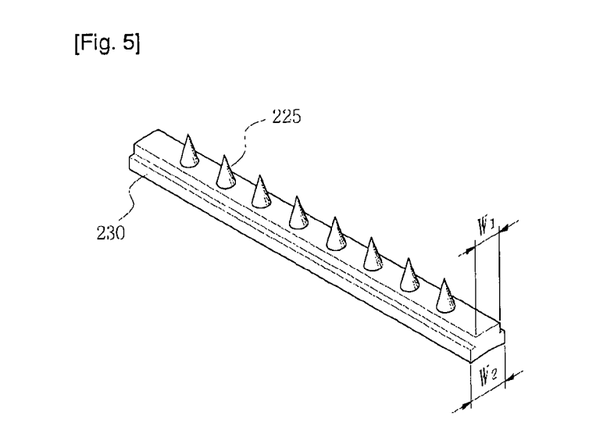
FIG. 5 is a perspective view of a needle block to be coupled with a roller head shown in FIG. 4.

FIG. 5 is a perspective view of one needle block 230 mounted to roller head 220.

The needle block 230 as shown in FIG. 5 is mounted to on the external cylindrical member 221 constituted as described above.

The needle block 230 is received in each groove 221-1 formed on an outer surface of the external cylindrical member 221. Accordingly, the needle block 230 and the groove 221-1 formed on the external cylindrical member 221 have the same general cross-sectional shape. That is, a width W2 of a lower portion of the needle block 230 is larger than a width W1 of an upper portion, and so the needle block 230 of the groove 221-1 may not be separated in the radial direction of the external cylindrical member 221. On the other hand, a height of each needle block 230 is the same as a depth of each groove 221-1 and a plurality of needles 225 are disposed on an upper surface of the needle block 230.

The needle block 230 and the needles 225 can be formed integrally with each other and made of polymer resin such as epoxy resin, phenol resin, polyurethane resin or thermoplastic resin such as PC (polycarbonate), PEI (polyetherimide), PMMA (polymethylmethacrylate), POM (polyacetal), PLA (polylatide), PSU (polysulfone) and the like.

Here, it is preferred to use biodegradable polymer, for example PLA (polylatide), PLGA (poly lactic-co-glycolic acid) as polymer resin. Due to the above material, if the needle 225 separated from the needle block 230 is remained in the skin, the needle made of the above mentioned material does not harm human being and can be dissolved in short time, Each needle 225 is protruded from an outer surface of the needle block 230 with a certain height. A height of the needle 225 may be varied according to a usage of the micro needle roller assembly 200. For example, if the needle 225 penetrates an epidermis to form a channel reaching a corium layer, a height of the needle 225 is in the range from 200 μm to 750 μm. In general, a height of the needle 225 is determined in the range from 20 μm to 2,000 μm, however, a height of the needle can be out of the above range, if necessary.

Here, the needles 225 can be disposed on the needle block 230 at regular intervals. Due to the above structure, the uniform channel distribution can be obtained on a specific area of the skin. However, in order to form a great number of the channels on a specific area of the skin through the needles 225, it is desirable to make narrow a distance between the needles 225 on the needle block 230. In addition, FIG. 5 shows that each needle 225 has a conical shape. However, a shape of the needle is not limited thereto.

As shown in FIG. 4, on the other hand, side covers 240 and 250 are mounted to both sides of the external member 221 for preventing the needle blocks 230 from being separated in an axial direction of the external member 221. Diameter of the side covers 240 and 250 are the same as that of the external member 221.

Once the side covers 240 and 250 are fixed to both sides of the external member 221, both end portions of the internal member 224 are exposed through openings 241 and 251 formed at central portions of the side covers 240 and 250 and both opened side ends of each groove 221-1 correspond to the side covers 240 and 250, respectively. In this state, the needle blocks 230 received in the grooves 221-1 can not be separated from the grooves by the side cover 240 or 250.

Below, an assembling process and a function of the needle roller assembly 200 according to this embodiment are described with reference to the drawing.

First, each of the needle blocks 230 is slid and inserted in respective groove 221-1 through an opened end of the groove 221-1 by pushing the needle block 230, and the side covers 240 and 250 are then fixed to both side end portions of the external member 221, respectively, after all the needle blocks are inserted in the grooves.

In this state, the protrusions 212A and 213A formed on the first and second connecting arms 212 and 213 of the handling member 210 are inserted into both end portions of the receiving space 224 of the internal member 222 of the roller head 220 exposed out of the side covers 240 and 250 to assemble the handling member 210 and the roller head 220.

Thereafter, the user grips the gripper 211 of the handling member 210 and places the external member 221 of the roller head 220 on a skin. In this state, once the users exerts a force to the gripper 211, the external member 221 is rotated about the protrusions 212A and 213A received in the receiving space 224 and moved on the skin.

The subsequent process and the function are the same as those of the needle roller assembly 100 according to the first embodiment, and so a detailed description thereto is omitted.

On the other hand, in a state where only one side cover (for example, 250) is fixed to one side end portion of the external member 221, the needle blocks 230 can be slid and inserted in the grooves 221-1 through opened ends of the groove 221-1 to which the side cover is not fixed. Then, another side cover (for example, 240) can be fixed to the other end portion of the external member 221 to complete an assembly of the roller head.

Figure 6:
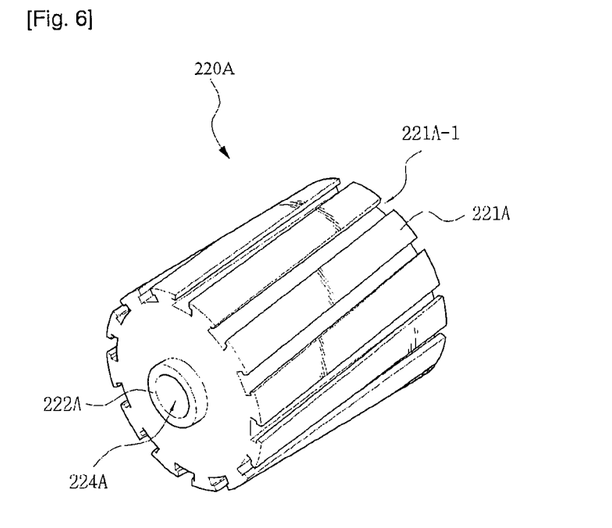
FIG. 6 is a perspective view of a modified example of the roller head shown in FIG. 4.

FIG. 6 is a perspective view of the modified example of the roller head shown in FIG. 4. Unlike the roller head 220 consisting of the external member 221 and the internal member 222 as shown in FIG. 4, single cylindrical member 221A having an axial through-passage 224A formed at a central portion thereof can be utilized as the roller head 220A.

In a case where single cylindrical member 221A is used as the roller head 220A, a plurality of grooves 221A-1 are formed on an outer surface of the cylindrical member 221A.

At this time, although the grooves 221A-1 can be formed in parallel to an axis of the cylindrical member 221A, each groove 221A-1 can be inclined at a certain angle with respect to an axis of the cylindrical member 221A as shown in FIG. 6. The needle blocks 230 are mounted to the needle head 220A having the structure as described above.

In the roller head 220A having the structure as shown in FIG. 6, on the other hand, due to a curved outer surface of the cylindrical member 221A, the grooves 221A-1 inclined at a certain angle with respect to an axis of the cylindrical member 221A has a longitudinal sectional shape which is rounded along the entire length thereof. As described above, however, since the needle block 230 is made of flexible resin material, although the groove 221A-1 has any shape, the needle block 230 having the elasticity can be smoothly inserted and received in the groove 221A-1.

Here, in the roller head 220 shown in FIG. 4, since the needle blocks 230 are disposed on the external member 221 at regular intervals, rows of the needles 225 are also disposed at regular intervals. In the roller head 220A having the structure shown in FIG. 6, however, each needle block 230 is inclinedly disposed with respect to the axis of the cylindrical member 221A so that the needles 225 are irregularly arranged on the roller head 220A.

Due to the above arrangement of the needles, in the needles formed on the same needle block 230, some of the needles penetrate the skin and the rest of the needles do not penetrate the skin. Accordingly, the roller head 220A can be smoothly rotated without generating a large resistance between the needle block and the skin.

Although not shown in the drawing, on the other hand, the side covers 240 and 250 shown in FIG. 4 are fixed to both sides of the roller head 220A to prevent the needle block 230 from be separated from the roller head 220A.

Third Embodiment

A micro needle roller assembly (hereinafter, referred to as "needle roller assembly" according to the third embodiment of the present invention is described as follows.

Figure 7:
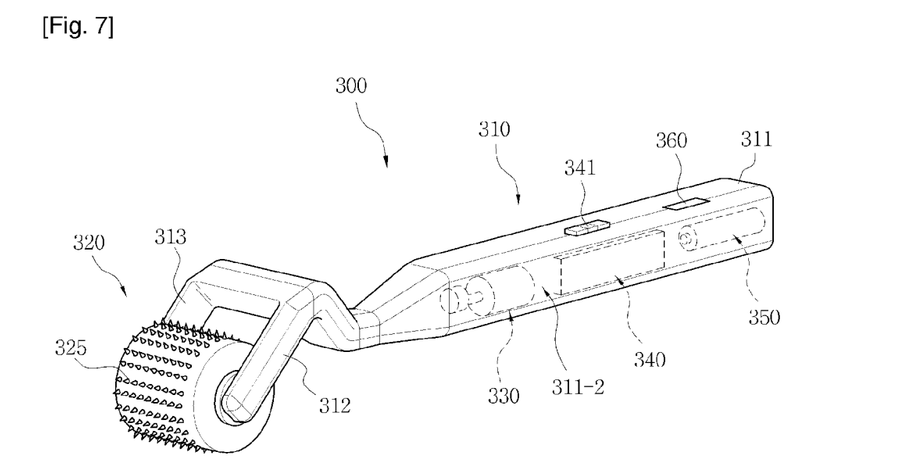
FIG. 7 is a perspective view of the micro needle roller assembly according to the third embodiment of the present invention.

FIG. 7 is a perspective view of a needle roller assembly according to the third embodiment of the present invention, a needle roller assembly 300 according the third embodiment of the present invention also comprises a roller head 320 and a handling member 310.

A structure and function of the roller head 320 in this embodiment are the same as those of the roller heads 220 and 220A according to the second embodiment, and so the description thereof is omitted.

In addition, a structure and function of needles 325 mounted to the roller head 320 in this embodiment are the same as those of the needles 125 and 225 mounted to the roller heads 120, 220 and 220A of the needle roller assemblies 100 and 200 according to the first and second embodiments, and so the description thereof is omitted.

Major feature of the needle roller assembly 300 according to the third embodiment of the present invention is the structure which can apply a vibration to the roller head 320 contacted with a skin to enhance the ability to penetrate the skin.

Below, the needle roller assembly 300 having the above function is described in more detail.

Figure 8:
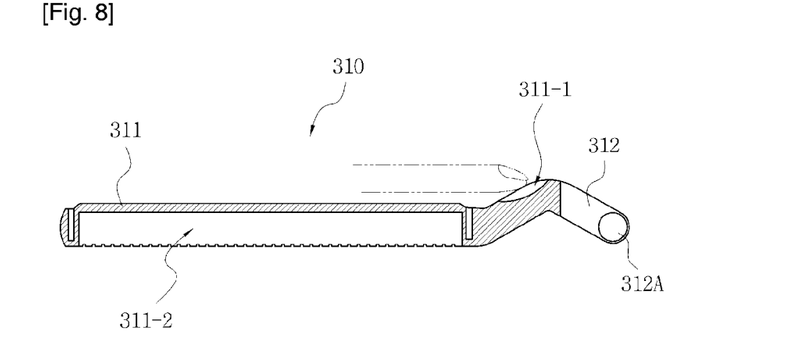
FIG. 8 is a sectional view of a handling member shown in FIG. 7.

FIG. 8 is a sectional view of the handling member 310 shown in FIG. 7, the handling member 310 comprises a gripper 311 and first and second connecting arms 312 and 313 extended from one end of the gripper 311 to both sides. Free ends of the first and second connecting arms 312 and 313 correspond to both side ends of the roller head 320. Cylindrical protrusions 312A and 313A (shown in FIG. 14) with a certain length are protrudely formed on inner surfaces of the free end portions of the first and second connecting arms 312 and 313, respectively, As shown in FIG. 8, an end portion of the gripper 311, that is, a portion adjacent to the first and second connecting arms 312 and 313 is inclined upward, a recess 311-1 with a certain depth is formed on the inclined portion. When the user uses the needle roller assembly 300, the user s finger is placed in the recess 311-1 formed on a front end portion of the gripper 311 so that the user can stably apply a force to the gripper 311.

As shown in FIG. 8, a space 311-2 with a certain volume can be formed in the gripper 311, a vibration generating means 330, a circuit section 340 and an electric power source 350 are accommodated in this space 311-2. A structure and function of the vibration generating means, the circuit section and the electric power source are described below.

Figure 9:
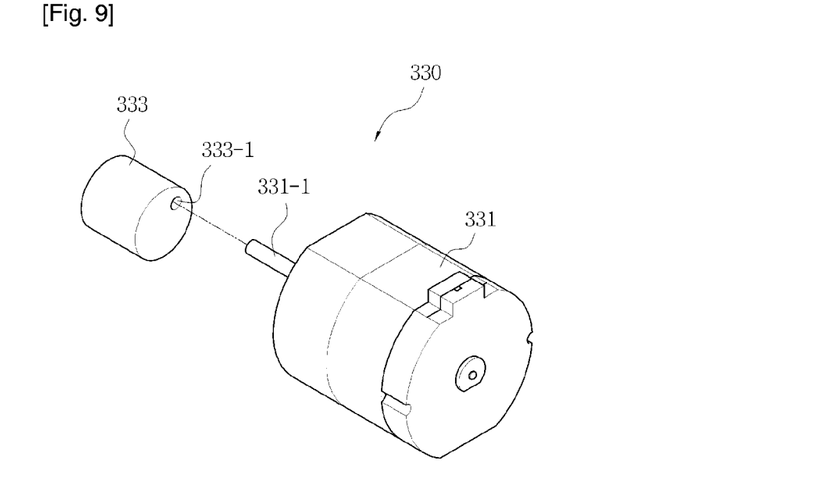
FIG. 9 is a perspective view of a motor and a vibration generating member utilized in the micro needle roller assembly according to the third embodiment of the present invention.

FIG. 9 is a view illustrating the vibration generating means constituting the needle roller assembly according to the third embodiment of the present invention, the vibration generating means 330 comprises a driving motor 331 and an eccentric weight 333.

As shown in FIG. 9, a connecting aperture 333-1 of the eccentric weight 333 to which a driving shaft 331-1 of the driving motor 331 is inserted to one side, and so a vibration is generated when the eccentric weight 333 is rotated according to a drive of the driving motor 331.

The vibration caused by the eccentric weight 333 is transmitted to the roller head 320 connected to the gripper 311 through the first and second connecting arms 312 and 313. Accordingly, the vibration is transmitted to the needles 325 mounted to the roller head 320 to make the needles 325 pierces easily the skin. Consequently, the drug penetrates effectively the skin.

In addition, the vibrating needles 325 stimulate the skin to activate a skin tissue and expedite a circulation of the blood, and so the drug penetrating in the skin can be effectively spread.

The circuit section 340 provided in the space 311-2 of the gripper 311 is electrically connected to the driving motor 331, a switch 341 (for example, a slide switch) connected to the circuit section 340 is slidably installed on an outer surface of the gripper 311. Thus, according to a movement of the switch 341, a flow of electric power to the driving motor 331 of the vibration generating means 330 is controlled through the circuit section 340.

The electric power source 350 (for example, a battery) is provided in the space 311-2 of the gripper 311, this electric power source 350 is electrically connected to the circuit section 340. According to an operation of the switch 341 described above, an electric power of the electric power source 350 is applied to the driving motor 331 of the vibration generating means 330 via the circuit section 340.

On the other hand, the needle roller assembly 300 according to the third embodiment of the present invention can further comprises a light emitting diode (LED) 360 provided on an outer surface of the gripper 311. For example, the LED 360 is electrically connected to the circuit section 340 and the driving motor 331 in series. Once the electric power is applied to the driving motor 331 through the circuit section 340, the LED 360 emits the light, and so the user can visually verify that the electric power is supplied to the driving motor 331.

Figure 10:
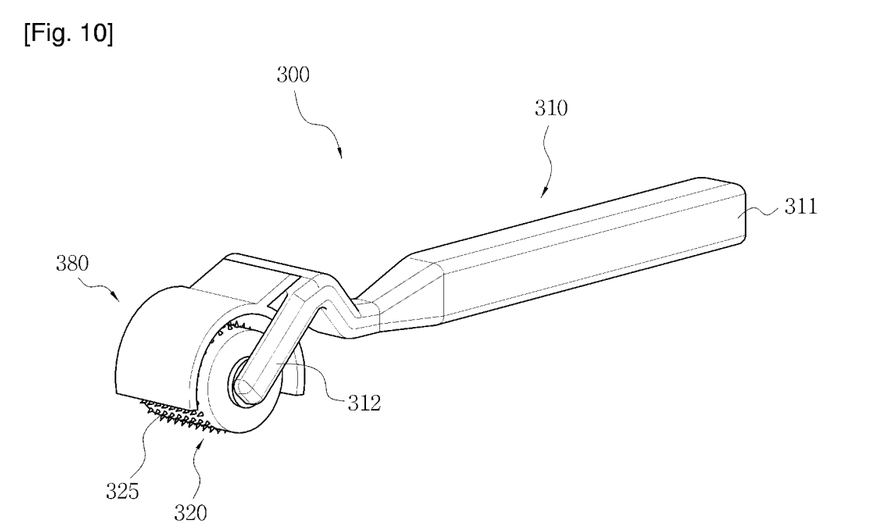
FIG. 10 is a perspective view of the micro needle roller assembly and shows that the cover is mounted to the roller head shown in FIG. 7.
Figure 11:
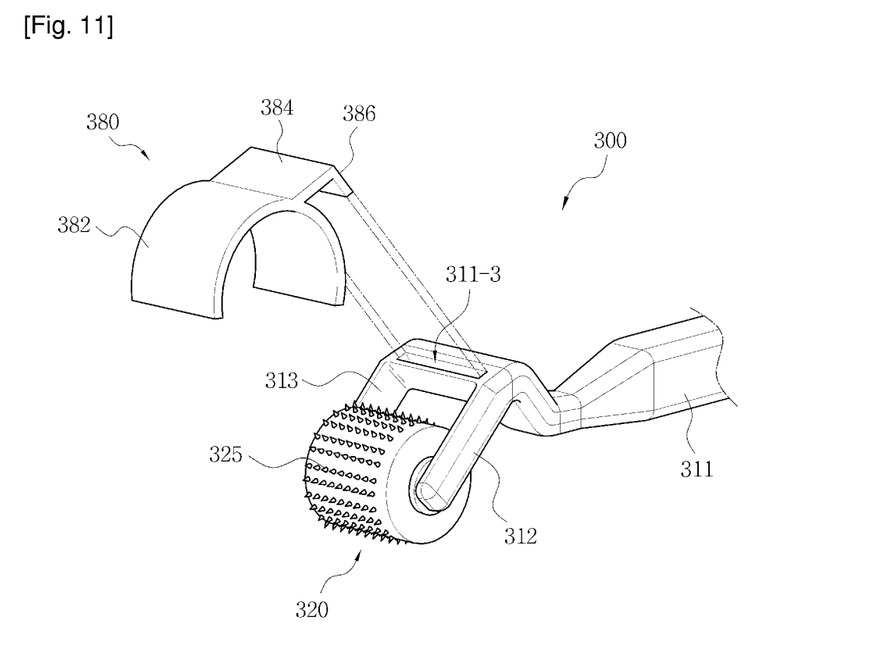
FIG. 11 is a partial perspective view showing a state where the cover is detached from the roller head shown in FIG. 10.

FIG. 10 is a perspective view of the needle roller assembly showing that a cover 380 is mounted to the roller head 320 shown in FIG. 7 and FIG. 11 is a partial perspective view showing a state where the cover 380 is detached from the roller head 320 shown in FIG. 10.

As described above, when the roller head 320 to which the needles 325 are mounted pressurizes the skin and is moved, blood can be spurted from channels formed by the needles 325. The cover 380 provided on the roller head 320 prevents blood from being splashed to an outside.

As shown in the drawing, the cover 380 comprises a hollow semi-cylindrical sheet 382, an extension piece 384 extended from the sheet 382 and a bending piece 386 formed at a rear end portion of the extension piece 384. A width of the sheet 382 is the same as that of the roller head 320.

On the other hand, a slit 311-3 with a certain width is formed on a front portion of the gripper 311 adjacent to the first and second connecting arms 312 and 313, the bending piece 386 of the cover 380 is inserted in this slit 311-3. Accordingly, the hollow semi-cylindrical sheet 382 of the cover 380 covers a portion of the roller head 320 except a lower side corresponding to the user's skin.

Figure 12:
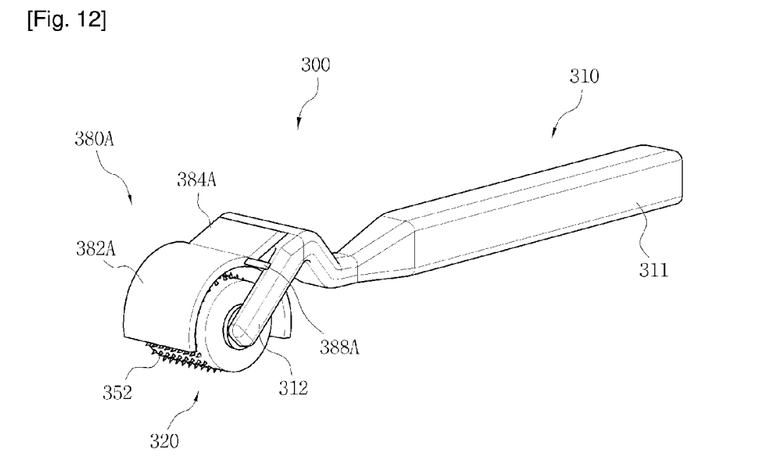
FIG. 12 and FIG. 13 are perspective views of the micro needles roller assemblies and shows the cover having the different shapes is mounted to the roller head.

FIG. 12 is a perspective view of the micro needles assembly and shows that a cover 380A is mounted to the roller head 320.

The cover 380A shown in FIG. 12 comprises a hollow semi-cylindrical sheet 382A, an extension piece 384A extended from the sheet 382A and a bending piece (not shown) formed at a rear end portion of the extension piece 384A. Supporting bars 388A with a certain length are fixed to both sides of the sheet 382A, the supporting bars 388A are contacted with upper surfaces of the first and second connecting arms 312 (in FIG. 12, only one supporting bar 388A and only one connecting arm 312 are shown).

The supporting bars 388A prevents the sheet 382A of the cover 380A from being contacted with the roller head 320, and so the roller head 320 can be smoothly rotated and moved without any obstruction caused by the sheet 382A.

Figure 13:
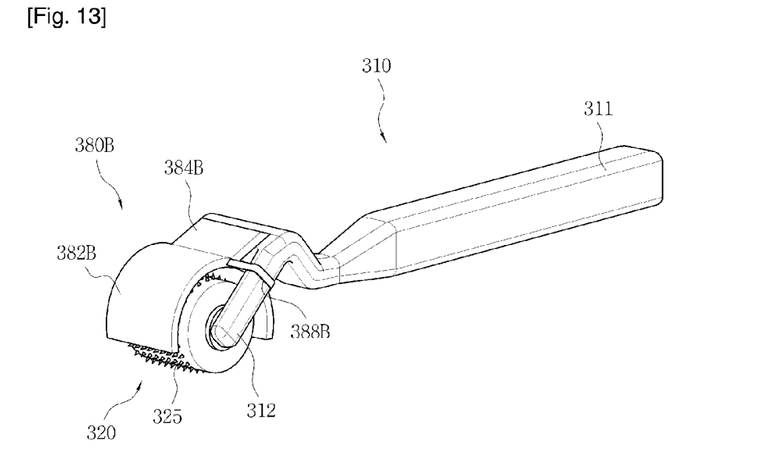

FIG. 13 is a perspective view of the micro needles assembly and shows that a cover 380B is mounted to the roller head 320. The cover 380B shown in FIG. 13 also comprises a hollow semi-cylindrical sheet 382B, an extension piece 384B extended from the sheet 382B and a bending piece (not shown) formed at a rear end portion of the extension piece 384B.

Hooks 388B with a certain length are fixed to both sides of the sheet 382B, the hooks 388B are coupled to the first and second connecting arms 312 (in FIG. 13, only one hook 388B and only one connecting arm 312 are shown).

The hooks 388B prevents the sheet 382B of the cover 380B from being contacted with the roller head 320, and so the roller head 320 can be smoothly rotated and moved without any obstruction caused by the sheet 382B.

On the other hand, grooves (not shown in the drawing) with a certain depth can be formed on upper surfaces of the first and second connecting arms 312, respectively, and each of these grooves corresponds to each hook. When the cover 380B is coupled to the roller head 320, the hooks 388B are received in the grooves formed on the upper surfaces of the first and second connecting arms 312, respectively, and so the hooks 388B can not be separated from the first and second connecting arms 312. Consequently, the cover 380B is stably placed on the roller head 320.

It is preferably that the covers 380, 380A and 380B described above is made of transparent material for enabling the user to verify visually whether blood is oozing from the channel formed by the needles or not. Polycarbonate (PC), polyethylene terephthalate (PET), polymethylmethacrylate (PMMA) and the like can be used as the material for the covers 380, 380A and 380B. Also, the cover can be formed integrally with the gripper.

Figure 14:
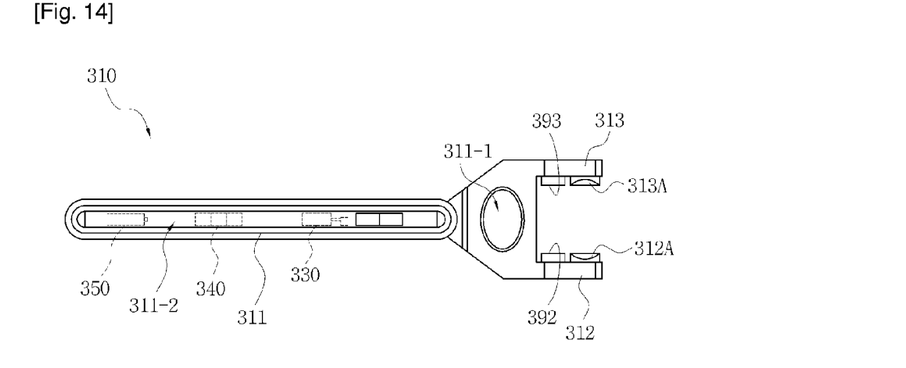
FIG. 14 is a plane view of the handling member in which an infrared ray-generating device is provided.

On the other hand, the needle roller assembly according to the present invention can further comprise at least one infrared ray-generating device. FIG. 14 is a plane view of the handling member in which the infrared ray-generating devices are mounted. For the convenience's sake, the roller head is not shown in FIG. 14.

The infrared ray-generating devices 392 and 393 are provided on inner surfaces of the first and second connecting arms 312 and 313 to be coupled to the roller head (320 in FIG. 7 to FIG. 13), the infrared ray-generating devices 392 and 393 are electrically connected to the electric power source 350 via the circuit section 340 described above.

Here, the circuit section 340, the vibration generation means 350 and the infrared ray-generating devices 392 and 393 are electrically and sequentially connected to each other and the circuit section 340 is connected to the vibration generation means 350 through the switch, and so the vibration generation means 350 and the infrared ray-generating devices 392 and 393 can be simultaneously controlled (that is, turned on/turned of) by an operation of the switch.

It is preferable to utilize the infrared ray-generating device radiating far infrared ray with a wavelength of 25 μm or more as the infrared ray-generating devices 392 and 393. As is generally known, far infrared ray has a high heat action and strong penetration force, and so it is possible to obtain an excellent fomentation effect for circulation of blood by means of far infrared ray. In addition, due to far infrared ray, skin can become soft so that the skin contacted with the needles is stimulated and the drug applied on the skin can easily penetrate the skin.

In general, far infrared ray radiating material discharged from the infrared ray-generating devices 392, 393 radiates more far infrared ray under a condition of a high temperature, and so it is desirable that the infrared ray-generating devices are heated to a temperature of 40 to 50° C. and then radiate the far infrared ray.

If far infrared ray of a temperature of 50° C. or more is radiated, it is apprehended that user can get burn in the skin. Accordingly, it is preferable that a temperature sensing sensor (not shown) is provided to control a temperature of far infrared ray to a pre-determined value or less.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and appended claims. In addition to variations and modifications in the component parts and/or arrangements, alternative uses will also be apparent to those skilled in the art.

INDUSTRIAL APPLICABILITY

Since all structural members, that is, the cylindrical external member and a plurality of needles formed on an outer surface of the external member and the internal member coupled to the external member by the supporting pieces are made of polymer resin and formed integrally with each other, the micro needle roller assembly according to the present invention can be simply manufactured by only once injection forming process.

In addition, in the micro needle roller assembly according to the present invention, the needle blocks on which the micro needles are formed and the roller head are separately manufactured and then assembled to each other. Accordingly, after the needle blocks that were contacted with the user's skin are detached from the roller head, new needle blocks are be then mounted to the roller head so that the roller head and the handling member can be repeatedly utilized.

Further, a plurality of needles having the different size (diameter and height) can be formed the needle blocks, respectively, and so the user can select the needle block having a desired sized needles on the basis of the kind of drug, a dosage of drug and a part of the body to which the drug is applied, and then mount the selected needle block to the roller head.

In particular, since the micro needle roller assembly according to the present invention comprises a vibration generating means, the micro needles pierces effectively skin due to a vibration transmitted to the roller head so that the drug delivery effect is increased, the skin tissue is activated and a circulation of blood can be expedited.

In addition, when the micro needles pierce the skin, blood spurted from channels formed by the needles is blocked by the cover placed on the roller head, and so the use can use sanitarily the micro roller assembly.

In particular, the skin can become soft by infrared ray radiated from the infrared ray-generating device to stimulate the skin contacted with the micro needles. Accordingly, the drug may be delivered in the skin to enhance remarkably a treatment effect.

What is claimed is:

1. A micro needle roller assembly, comprising:
a roller head including:
an external cylindrical member comprising a plurality of grooves formed in a longitudinal direction on a surface of the external cylindrical member and a plurality of micro needle blocks mounted in the plurality of grooves, each micro needle block of the plurality of micro needle blocks being configured to be mounted in one of the plurality of grooves, each micro needle block comprising a plurality of micro needles, and the plurality of micro needles being made of a polymer resin;
an internal member positioned inside the external cylindrical member, the internal member comprising two end portions and a receiving space formed at each of the end portions; and
a plurality of supporting pieces securing the internal member to the external member; and
a handling member coupled to the internal member and configured to rotate the internal member of the roller head, the handling member comprising:
a gripper with a slit formed at a portion thereof;
a first connecting arm having an inner surface and a protrusion formed on the inner surface;
a second connecting arm having an inner surface and a protrusion formed on the inner surface of the second connecting arm, the first connecting arm and the second connecting arm both extending from the gripper, each protrusion of the first and second connecting arms being received in a corresponding receiving space of the internal member of the roller head;
a power electric source received in a space formed in the gripper of the handling member;
a vibration generator received in the space formed in the gripper of the handling member;
first and second infrared ray-generating devices connected to the power electric source via a switch, the first and second infrared ray-generating devices positioned on the inner surfaces of the first and second connecting arms respectively; and
a cover detachably fixed to the gripper and placed on the roller head, and the cover comprises:
a hollow semi-cylindrical sheet,
an extension piece extended from the sheet, and
a bending piece formed at one end portion of the extension piece and inserted in the slit of the gripper,
wherein the plurality of supporting pieces extend in a radial direction of the internal member, a total number of supporting pieces of the plurality of supporting pieces is the same as a total number of grooves of the plurality of grooves of the external cylindrical member,
wherein first, second, third, and fourth supporting pieces of the plurality of supporting pieces are positioned to align behind in the radial direction, respectively, first, second, third, and fourth grooves of the plurality of grooves of the external cylindrical member, such that each groove of the plurality of grooves is aligned in front, in the radial direction, of each respective supporting piece of the plurality of supporting pieces.

2. The micro needle roller assembly according to claim 1, further comprising:
at least one supporting bar fixed to at least one side of the sheet and contacted with upper sides of the first and second connecting arms.

3. The micro needle roller assembly according to claim 2, wherein the vibration generator comprises a driving motor connected electrically to the power electric source and comprises an eccentric weight coupled to a driving shaft of the driving motor.

4. The micro needle roller assembly according to claim 2, further comprising the switch for controlling an electrical connection between the vibration generator and the power electric source.

5. The micro needle roller assembly according to claim 2, wherein the gripper has a recess formed on a surface thereof adjacent to the first and second connecting arms.

6. The micro needle roller assembly according to claim 2, wherein the first infrared ray-generating device applies infrared rays with a wavelength of at least 250 µm.

7. The micro needle roller assembly according to claim 1, wherein each groove of the plurality of grooves has an upper portion and a lower portion having a width larger than that of the upper portion, and each micro needle block of the plurality of micro needle blocks has a sectional shape that is the same as that of each groove of the plurality of grooves.

8. The micro needle, roller assembly according to claim 1, wherein the external cylindrical member is made of a polymer resin.

9. The micro needle roller assembly according to claim 1, wherein the internal member is a hollow cylindrical member.

10. The micro needle roller assembly according to claim 1, wherein the receiving spaces are cylindrically shaped.

11. The micro needle roller assembly according to claim 1, wherein each supporting piece of the plurality of supporting pieces has a length that is the same as that of the external member to prevent the external member from being transformed.

12. The micro needle roller assembly according to claim 1, wherein the external cylindrical member is made from a same material from which the plurality of micro needle blocks are made.

13. The micro needle roller assembly according to claim 1, wherein the grooves of the plurality of grooves are formed parallel to an axis of the external cylindrical member.

14. The micro needle roller assembly according to claim 1, wherein the grooves of the plurality of grooves are inclined at an angle with respect to an axis of the external cylindrical member.

15. The micro needle roller assembly according to claim 1, wherein the sheet of the cover has a width that is the same as that of the roller head.

16. The micro needle roller assembly according to claim 1, further comprising side covers fixed to both side ends of the roller head, the side covers positioned and configured to prevent the plurality of micro needle blocks from sliding out through an opened end of the plurality of grooves.

17. The micro needle roller assembly according to claim 1, wherein each micro needle block of the plurality of micro needle blocks comprises the plurality of micro needles integrally formed therewith.

18. The micro needle roller assembly according to claim 17, wherein the plurality of micro needles is made of a same material as each micro needle block of the plurality of micro needle blocks, the material being the polymer resin.

19. The micro needle roller assembly according to claim 18, wherein the polymer resin is one of a thermosetting resin and a thermoplastic resin.

20. The micro needle roller assembly according to claim 18, wherein the polymer resin is a biodegradable polymer.

* * * * *